United States Patent [19]

Takayama et al.

[11] 4,322,498

[45] Mar. 30, 1982

[54] CITRIC ACID PRODUCING MUTANT YEAST STRAINS

[75] Inventors: Kenichiro Takayama, Machida; Tetsuo Adachi, Tokyo; Mamoru Kohata, Kawasaki; Kiyoji Hattori, Machida; Tomoko Tomiyama, Tokyo, all of Japan

[73] Assignee: Kyowa Hakko Kogyo Co., Ltd., Tokyo, Japan

[21] Appl. No.: 515,212

[22] Filed: Oct. 16, 1974

Related U.S. Application Data

[62] Division of Ser. No. 452,405, Mar. 18, 1974, Pat. No. 3,926,724.

[51] Int. Cl.$^3$ .............................................. C12N 1/16
[52] U.S. Cl. .................................. 435/255; 435/144; 435/921

[58] Field of Search ............... 195/28 R, 29, 36, 37 R, 195/47, 112, 114; 435/255, 921, 144, 172

[56] References Cited

U.S. PATENT DOCUMENTS

3,118,821  1/1964  Clark ................................... 195/114

FOREIGN PATENT DOCUMENTS

2005848  of 1970  Fed. Rep. of Germany .... 195/28 R

*Primary Examiner*—R. B. Penland
*Attorney, Agent, or Firm*—Fitzpatrick, Cella, Harper & Scinto

[57] ABSTRACT

Citric acid is selectively produced by fermentation of a mutant yeast strain which requires the presence of iron in the culture medium. Citric acid is accumulated in the culture medium and isolated therefrom.

4 Claims, No Drawings

CITRIC ACID PRODUCING MUTANT YEAST STRAINS

This is a division of application Ser. No. 452,405, filed Mar. 18, 1974, U.S. Pat. No. 3,926,724.

BACKGROUND OF THE INVENTION

The present invention relates to the selective production of citric acid and more specifically to the production of citric acid by fermentation of a mutant yeast strain which requires the presence of iron within the culture medium.

Citric acid has wide uses and is useful for example, for the preparation of beverages and pharmaceutical syrups.

Heretofore, there have been proposed in the art various processes for the production of citric acid using yeasts. When citric acid is produced by fermentation using yeasts, usually, a considerable amount of isocitric acid occurs in the culture medium as a by-product. Isocitric acid is an organic acid for which there is not a significant amount of commercial use. Thus, it is rarely desired to produce isocitric acid. Moreover, the by-production of isocitric acid renders isolation and purification of citric acid from the culture medium very complicated.

On the other hand, it is known that the production of isocitric acid in a fermentation process is accelerated by the presence of iron ion or iron-containing ion such as $Fe(CN)_6^{-4}$ [Journal of the Agricultural Chemical Society of Japan, Vol. 44, p. 562 (1970), Japan and U.S. Pat. No. 3,773,620]. Therefore, in order to prevent the by-production of isocitric acid, it is necessary that iron ion or iron-containing ion be absent from the medium. However, from a commercial standpoint, contamination of the medium by iron ion is unavoidable due to the fermentation raw materials and equipment. For example, in the commercial production of citric acid, usually an apparatus made of stainless steel or one having a glass lining is used. In either case, contamination of the medium with iron ion is unavoidable. Even the slight contamination of the medium due to the apparatus is considered to be sufficient to cause a significant production of isocitric acid and, therefore, renders the process impractical.

U.S. Pat. No. 3,689,359 discloses that a citric acid-accumulating yeast belonging to the genus Candida which is incapable of utilizing citric acid suppresses production of isocitric acid while producing a high yield of citric acid. However, this process also suffers from serious drawbacks, and a more practical method is still in demand.

Accordingly, the present invention is concerned with the suppression of the by-production of isocitric acid in a fermentation process while maintaining the production of citric acid in a yield equal to or greater than that of the same process with the by-production of isocitric acid. In such manner, a commercially feasible process is attained which substantially eliminates the heretofore necessary step of purification of the citric acid.

DESCRIPTION OF THE INVENTION

In accordance with the present invention, it has been found that mutant yeast strains which require a higher amount of iron for growth as good as that of the parent strains by-produce no substantial amount of isocitric acid and produce citric acid in a yield equal to or even higher than the yield of citric acid produced by the parent strain. Such mutants, therefore, have a nutritional requirement for iron.

"Nutrition-requirement" is a term well known in microbiology. A nutrition-requiring mutant means a mutant that can not grow as well as that of the parent strain in a minimum medium in which the parent strain can grow but can grow as well as that of the parent strain in the minimum medium to which a specific nutrient is added. Such mutants are sometimes referred to as auxotrophic mutants, an auxotrophic mutant being a mutant that requires growth factors not needed by the parent cells.

In the present specification, "requirement for iron" means that the requirement is satisfied with the presence of iron ion or iron-containing ion, and, more practically, with the addition of a compound that results in the presence of iron ion or iron-containing ion in the medium.

The mutants useful in the present invention require iron. However, whether the parent strains of the mutants of the present invention require iron or not is difficult to determine since it is impossible to culture a strain in the absolute absence of iron ion. The contamination of the medium by iron ion due to, for example, fermentation raw materials and an apparatus made of glass is unavoidable. Therefore, for the purposes of the present invention, it is to be understood that the parent strains of the mutants can show sufficient growth in a medium to which no source of iron is intentionally added. Accordingly, even if the parent strains require iron for growth, the amount of iron required is only a trace. On the other hand, the mutants of the present invention can not exhibit as good growth as that of the parent strains in a medium to which no source of iron is intentionally added but their growth is comparable to that of the parent strains only in a medium containing a source of iron intentionally added to the medium. Thus, as used therein, the mutants of the invention are described not as "requiring iron" but are expressed as "requiring a higher amount of iron".

The mutants contemplated in the present invention usually exhibit a growth comparable to that of the parent strains in the presence of 0.1 mg/L, and preferably, 0.2 mg/L or more of iron. Particularly preferred mutants of the invention are *Candida zeylanoides* T-15, ATCC 20391; T-20, ATCC 20392; T-57, ATCC 20393 and IC 142, ATCC 20367, all of which are derived from *Candida zeylanoides* No. 19-5, ATCC 20347. These mutants are deposited with American Type Culture Collection, Rockville, Md., U.S.A., and are freely available to the public. The aforementioned strains require a higher amount of iron for growth than the parent strain. *Candida zeylanoides* IC 142, ATCC 20367 requires glycerin for growth in addition to an iron requirement.

To further illustrate the intended nutritional requirement of the mutants suitable for the present invention, *Candida zeylanoides* T-15, ATCC 20391; T-20, ATCC 20392; T-57, ATCC 20393; and IC 142, ATCC 20367 are cultured and compared to *Candida zeylanoides* No. 19-5, ATCC 20347 as a control. A basal medium having the following composition is prepared.

| | |
|---|---|
| glucose | 30 g/L |
| NH$_4$Cl | 3 g/L |
| KH$_2$PO$_4$ | 0.5 g/L |
| MgSO$_4$ . 7H$_2$O | 0.5 g/L |
| MnSO$_4$ . 4H$_2$O | 2 mg/L |

-continued

| | |
|---|---|
| $ZnSO_4 \cdot 7H_2O$ | 2 mg/L |
| $CuSO_4 \cdot 5H_2O$ | 50 μg/L |
| thiamine hydrochloride | 100 μg/L |
| $CaCO_3$ | 10 g/L |
| glycerin (in the case of the IC 142, ATCC 20367 strain only) | 0.5 g/L |
| (pH 7.0) | |

To the basal medium is added $FeSO_4 \cdot 7H_2O$ in various concentrations, i.e. 0.25 mg/L (about 0.05 mg/L iron ion), 0.5 mg/L (about 0.1 mg/L iron ion), 1 mg/L (about 0.2 mg/L iron ion), 2.5 mg/L (about 0.5 mg/L iron ion) and 5 mg/L (about 1.0 mg/L iron ion). Each of the strains to be tested is cultured on a malt extract agar slant, prepared by dissolving 4 g glucose, 4 g yeast extract and 10 g malt extract in water to make up a volume of 1 L and adjusting the pH to 7.0, at 30° C. for 24 hours. The resulting cultures are suspended in physiological sodium chloride solutions. The suspensions are transferred to 10 ml of the basal medium and the nutritionally supplemented media, each in a large test tube, at a concentration of $10^7$ cells/ml. Culturing is carried out with shaking at 30° C. for 48 hours. After the completion of culturing, the amount of growth is determined by measuring the optical density of the culture liquor at a wave length of 660 mμ. The results are shown in Table 1.

TABLE 1

| Strains | Growth concentration of iron ion | | | | | |
|---|---|---|---|---|---|---|
| | 0 | 0.05 mg/L | 0.1 mg/L | 0.2 mg/L | 0.5 mg/L | 1.0 mg/L |
| T-15, ATCC 20391 | 5.2 | 8.0 | 12.0 | 12.8 | 13.0 | 14.0 |
| T-20, ATCC 20392 | 5.1 | 8.5 | 12.2 | 12.9 | 13.0 | 13.8 |
| T-57, ATCC 20393 | 5.0 | 9.0 | 12.4 | 13.0 | 13.2 | 14.0 |
| IC 142, ATCC 20367 | 4.5 | 7.0 | 12.2 | 12.5 | 13.0 | 13.8 |
| No. 19-5, ATCC 20347 | 13.3 | — | — | 13.5 | 14.2 | 14.4 |

It is apparent from the above Table 1 that each of the mutant strains of *Candida zeylanoides*, i.e. T-15, ATCC 20391; T-20, ATCC 20392; T-57, ATCC 20393 and IC 142, ATCC 20367 exhibits growth of about 90% of that of the parent strain (ATCC 20347) in the presence of at least 0.1 mg/L of iron and shows as good growth as that of the parent strain in the presence of 0.2 mg/L or more of iron.

Although the preferred mutants are derived from *Candida zeylanoides*, it is to be understood that any yeast which is capable of producing citric acid may be mutated to require a higher amount of iron for growth; and such mutants are suitable for the present invention. Generally speaking, suitable yeasts are found within the family Cryptococcaceae, and the genus Candida. Such yeasts are generally characterized by multipolar budding, forming pseudomycelium and occasionally mycelium, being fermentative.

In obtaining mutants requiring a higher amount of iron suitable for the present invention, any of the conventional methods for inducing mutation to obtain a strain having a requirement property may be employed. For example, such artificial mutation means as X-ray irradiation, ultraviolet ray irradiation, nitrogen-mustard treatment, nitrosoguanidine treatment, etc. are appropriate. As an example, microbial cells of a yeast strain are suspended in trismaleate buffer solution having a pH of 9.0 containing 200 γ/ml of N-methyl-N'-nitro-N-nitrosoguanidine at a concentration of $10^8$ cells per 1 ml. The suspension is allowed to stand for 15 minutes. The cells are then collected by centrifugation, washed with sterile physiological sodium chloride solution, placed on an agar plate and incubated.

The resulting colonies are isolated into pure cultures by any of the well known methods. Each of the pure cultures is then tested against the parent strain in a manner such as described above; and those strains which have been mutated to acquire the desired iron requirement are selected as applicable for the process of the invention.

Any culture medium normally used for the culturing of yeasts is suitable for the present invention as long as it contains an assimilable carbon source, a nitrogen source, inorganic materials and other growth promoting factors which may be required by the specific yeast strain used.

As the carbon source, hydrocarbons, such as n-paraffins and kerosene, carbohydrates such as glucose and blackstrap molasses and acetic acid are suitable. As the nitrogen source, inorganic compounds such as ammonium chloride, ammonium sulfate, ammonium nitrate, ammonium phosphate and ammonium acetate, urea and nitrogen-containing natural substances such as peptone, meat extract and corn steep liquor may be used. Additionally, as inorganic materials, potassium dihydrogen phosphate, magnesium sulfate, manganese sulfate, ferrous sulfate, ferric chloride and zinc sulfate may be used.

Although ferrous sulfate and ferric chloride are preferred sources of iron ion in the culture medium, any soluble iron salt which does not prove toxic to the microorganism is appropriate.

As the source of iron-containing ion, potassium ferrocyanide, sodium ferrocyanide, potassium ferricyanide, sodium ferricyanide and iron alum may be used.

Culturing is carried out under aerobic conditions at 20° to 40° C., and at a slightly acidic to neutral pH of about 3–7 for 2 to 5 days, at which time a considerable amount of citric acid is formed in the culture liquor. The pH may be adjusted with calcium carbonate, sodium hydroxide or an aqueous ammonia.

After the completion of culturing, the microbial cells are removed from the culture liquor by, for example, filtration and the filtrate is concentrated. By adding calcium hydroxide to the filtrate, citric acid is readily recovered as calcium citrate. The calcium citrate is converted to citric acid by the addition of sulfuric acid, thus precipitating out calcium sulfate. Of course, the citric acid may also be recovered by any other of the usually used purification techniques.

Practice of specific embodiments of the invention is illustrated by the following representative examples.

EXAMPLE 1

In this example, *Candida zeylanoides*, T-15, ATCC 20391; T-20, ATCC 20392 and T-57, ATCC 20393, each requiring at least 0.1 mg/L of iron, are used. As a control *Candida zeylanoides* No. 19-5, ATCC 20347 which does not have the iron requiring property is used. Each of the strains is cultured on a malt extract agar slant prepared by dissolving 4 g glucose, 4 g yeast extract and 10 g malt extract in water to make up a total volume of 1 L and adjusting the pH of the solution to 7.0, at 30° C. for 24 hours. The resulting cultures are inoculated into 20 ml portions of a seed medium having the following composition in a 250 ml-Erlenmeyer flask provided with baffle plates.

| n-paraffins | 30 ml/L |
|---|---|
| NH$_4$Cl | 5 g/L |
| KH$_2$PO$_4$ | 0.5 g/L |
| MgSO$_4$ . 7H$_2$O | 0.5 g/L |
| MnSO$_4$ . 4H$_2$O | 2 mg/L |
| ZnSO$_4$ . 7H$_2$O | 2 mg/L |
| FeSO$_4$ . 7H$_2$O | 1 mg/L |
| CuSO$_4$ . 5H$_2$O | 50 µg/L |
| thiamine hydrochloride | 100 µg/L |
| CaCO$_3$ (separately sterilized) | 10 g/L |
| (pH 6.0) | |

Culturing is carried out with shaking at 200 r.p.m. at 30° C. for 24 hours. 2 ml of each of the seed cultures is then inoculated into 20 ml of a fermentation medium in a 250 ml-Erlenmeyer flask provided with baffle plates. The fermentation medium comprises:

| n-paraffins | 100 ml/L |
|---|---|
| NH$_4$Cl | 5 g/L |
| KH$_2$PO$_4$ | 0.5 g/L |
| MgSO$_4$ . 7H$_2$O | 0.5 g/L |
| MnSO$_4$ . 4H$_2$O | 2 mg/L |
| ZnSO$_4$ . 7H$_2$O | 2 mg/L |
| FeSO$_4$ . 7H$_2$O | 10 mg/L |
| CuSO$_4$ . 5H$_2$O | 50 µg/L |
| thiamine hydrochloride | 100 µg/L |
| CaCO$_3$ (separately sterilized) | 80 g/L |
| (pH 6.0) | |

Fermentation is then carried out with shaking at 200 r.p.m. at 30° C. for 96 hours. The results are shown in Table 2.

TABLE 2

| Strains | Citric acid (mg/ml) | Isocitric acid (mg/ml) |
|---|---|---|
| T-15, ATCC 20391 | 77 | 2.0 |
| T-20, ATCC 20392 | 84 | 3.7 |
| T-57, ATCC 20393 | 77 | 2.9 |
| No. 19-5, ATCC 20347 | 48 | 30.0 |

EXAMPLE 2

In this example, *Candida zeylanoides* IC 142, ATCC 20367, which requires at least 0.1 mg/L iron and *Candida zeylanoides* No. 19-5, ATCC 20347 are each cultured on a malt extract agar slant prepared in the same manner as described in Example 1 at 30° C. for 24 hours. The resulting cultures are inoculated into 20 ml portions of a seed medium having the same composition as that of Example 1, except for additionally containing 5 g/L of glycerin, in a 250 ml-Erlenmeyer flask provided with baffle plates. Culturing is carried out with shaking at 200 r.p.m. at 30° C. for 24 hours. 2 ml of the seed cultures is then inoculated into 20 ml portions of a fermentation medium in a 250 ml-Erlenmeyer flask provided with baffle plates. The fermentation medium comprises:

| n-paraffins | 100 ml/L |
|---|---|
| glycerin | 1 g/L |
| NH$_4$Cl | 5 g/L |
| KH$_2$PO$_4$ | 0.5 g/L |
| MgSO$_4$ . 7H$_2$O | 0.5 g/L |
| MnSO$_4$ . 4H$_2$O | 2 mg/L |
| ZnSO$_4$ . 7H$_2$O | 2 mg/L |
| FeSO$_4$ . 7H$_2$O | 0-100 mg/L* |
| CuSO$_4$ . 5H$_2$O | 50 µg/L |
| thiamine hydrochloride | 100 µg/L |
| CaCO$_3$ (separately sterilized) | 80 g/L |
| (pH 6.0) | |

*FeSO$_4$ . 7H$_2$O is added in various amounts, as indicated in Table 3 below.

Fermentation is carried out with shaking at 200 r.p.m. at 30° C. for 96 hours. The results are shown in Table 3.

TABLE 3

| Strains | FeSO$_4$ . 7H$_2$O (mg/L) | Citric acid (mg/ml) | Isocitric acid (mg/ml) |
|---|---|---|---|
| IC 142, ATCC 20367 | 0 | 65 | 0.8 |
|  | 0.2 | 68 | 0.8 |
|  | 1 | 70 | 2.0 |
|  | 10 | 73 | 3.2 |
|  | 20 | 71 | 4.5 |
|  | 100 | 70 | 8.0 |
| No. 19-5, ATCC 20347 | 0 | 58 | 12.0 |
|  | 1 | 52 | 18.0 |
|  | 10 | 42 | 26.0 |
|  | 100 | 40 | 30.5 |

EXAMPLE 3

In this example, *Candida zeylanoides* IC 142, ATCC 20367 and No. 19-5, ATCC 20347 are cultured on malt extract agar slants prepared in the same manner as described in Example 1 at 30° C. for 24 hours. Three loopfuls of the resulting cultures are each inoculated into 200 ml of a seed medium having the same composition as that of Example 2 in 2 L-Erlenmeyer flasks provided with baffle plates and cultured at 30° C. for 24 hours with shaking. 300 ml of the resulting cultures (corresponding to the volume of 1.5 flasks) is inoculated into 3 L portions of a fermentation medium in 5 L-jar fermenters. The fermentation medium has the same composition as that of Example 2 containing 1 mg/L of FeSO$_4$.7H$_2$O except for not containing CaCO$_3$. Fermentation is carried out with stirring at 600 r.p.m. and aeration of 3 L/min. at 30° C. for 90 hours. During fermentation, the pH of the medium is adjusted to 6.0 with aqueous ammonia. The results are shown in Table 4.

TABLE 4

| Strains | Citric acid (mg/ml) | Isocitric acid (mg/ml) |
|---|---|---|
| IC 142, ATCC 20367 | 105.0 | 3.0 |
| No. 19-5, ATCC 20347 | 84.0 | 18.0 |

3 L of the culture liquor obtained by culturing IC 142, ATCC 20367 and containing 315 g of citric acid is subjected to filtration to remove the microbial cells. To the cell-free culture liquor is added 200 g of calcium hydroxide. As a result, 350 g of calcium citrate is obtained.

EXAMPLE 4

In this example, *Candida zeylanoides* IC 142, ATCC 20367 and No. 19-5, ATCC 20347 are used. Known citric acid producing strains of *Candida lipolytica* ATCC 20237, Candida sp. ATCC 20238, Candida sp. ATCC 20239, Candida sp. ATCC 20241 and *Candida tropicalis* ATCC 20240, all of which are disclosed in U.S. Pat. No. 3,689,359, are also used. Each of the strains is cultured on a malt extract agar slant prepared in the same manner as described in Example 1 at 30° C. for 24 hours. Samples of resulting cultures are inoculated into 20 ml portions of a seed medium in 250 ml-Erlenmeyer flasks provided with baffle plates. The seed medium has the same composition as that of Example 2 except for containing 50 μg/L thiamine hydrochloride and 20 g/L $CaCO_3$. Seed culturing is carried out with shaking at 200 r.p.m. at 30° C. for 24 hours. Then, 2 ml portions of the resulting seed cultures are inoculated into 20 ml portions of two kinds of fermentation media (Media A and B) in 250 ml-Erlenmeyer flasks. Medium A is of the same composition as that of Example 1 except for containing no $FeSO_4.7H_2O$. Medium B is also of the same composition as that of Example 1 except for containing 500 mg/L of $FeSO_4.7H_2O$. Fermentation is carried out with shaking at 200 r.p.m. at 30° C. for 120 hours. The results are shown in Table 5 (Medium A) and Table 6 (Medium B).

TABLE 5

| Strains | Medium A: $FeSO_4.7H_2O$: 0 mg/L | |
|---|---|---|
|  | Citric acid (mg/ml) | Isocitric acid (mg/ml) |
| IC 142, ATCC 20367 | 87.1 | 3.0 |
| No. 19-5, ATCC 20347 | 77.0 | 30.0 |
| ATCC 20237 | 73.9 | 12.4 |
| ATCC 20238 | 5.0 | 1.5 |
| ATCC 20239 | 4.8 | 1.4 |
| ATCC 20240 | 24.1 | 4.1 |
| ATCC 20241 | 65.2 | 31.8 |

TABLE 6

| Strains | Medium B: $FeSO_4.7H_2O$: 500 mg/L | |
|---|---|---|
|  | Citric acid (mg/ml) | Isocitric acid (mg/ml) |
| IC 142, ATCC 20367 | 95.5 | 13.8 |
| No. 19-5, ATCC 20347 | 36.7 | 32.2 |
| ATCC 20237 | 59.4 | 21.0 |
| ATCC 20238 | 10.1 | 7.4 |
| ATCC 20239 | 6.2 | 7.7 |
| ATCC 20240 | 25.8 | 17.0 |
| ATCC 20241 | 37.0 | 46.2 |

EXAMPLE 5

In this example, *Candida zeylanoides* IC 142, ATCC 20367 and *Candida lipolytica* ATCC 20237 (disclosed in U.S. Pat. No. 3,689,359) are individually inoculated into 20 ml of a first seed medium having the following composition in a 250 ml-Erlenmeyer flask.

| | |
|---|---|
| n-paraffins | 30 ml/L |
| $KH_2PO_4$ | 1 g/L |
| $(NH_4)_2SO_4$ | 4 g/L |
| $MgSO_4.7H_2O$ | 5 g/L |
| KCl | 0.1 g/L |
| NaCl | 1 g/L |
| thiamine hydrochloride | 300 μg/L |
| $CaCO_3$ | 10 g/L |
| glycerin (In the case of the IC 142, ATCC 20367 strain only) (pH 6.0) | 5 g/L |

Culturing is carried out with shaking at 30° C. for 48 hours. The thus obtained first seed cultures are transferred to 300 ml portions of a second seed medium having the same composition as that of the first seed medium in 2 L-Erlenmeyer flasks and cultured at 30° C. for 48 hours. The second seed cultures are transferred to 3 L portions of a third seed medium having the same composition as that of the first seed medium in 5 L-jar fermenters and cultured at 30° C. for 24 hours. 300 ml portions of the third seed culture are then inoculated into 3 L portions of fermentation media C and D having the following composition, respectively in 5 L-jar fermenters.

| | Medium C | Medium D |
|---|---|---|
| n-paraffins | 100 ml/L | 100 ml/L |
| $KH_2PO_4$ | 0.25 g/L | 0.5 g/L |
| $(NH_4)_2SO_4$ | 4 g/L | — |
| $NH_4Cl$ | — | 5 g/L |
| $MgSO_4.7H_2O$ | 0.5 g/L | 0.5 g/L |
| KCl | 0.5 g/L | — |
| NaCl | 0.1 g/L | — |
| $ZnSO_4.7H_2O$ | 1 mg/L | 2 mg/L |
| $CuSO_4.5H_2O$ | 100 μg/L | 50 μg/L |
| $FeSO_4.7H_2O$ | 100 mg/L | 100 mg/L |
| $MnSO_4.4H_2O$ | — | 2 mg/L |
| thiamine hydrochloride | 50 μg/L | 50 μg/L |
| $CaCO_3$ | 1 g/L | — |

Fermentation is carried out with stirring at 600 r.p.m. and aeration of 3 L/min. at 30° C. for 96 hours while adjusting the pH to 6.0 with aqueous ammonia. The results are shown in Table 7.

TABLE 7

| Strains | Medium | Culturing period (hours) | Citric acid (mg/ml) | Isocitric acid (mg/ml) |
|---|---|---|---|---|
| IC 142, ATCC 20367 | C | 72 | 85.9 | 12.2 |
|  |  | 96 | 87.7 | 11.4 |
|  | D | 72 | 88.6 | 6.8 |
|  |  | 96 | 101.9 | 4.2 |
| ATCC 20237 | C | 72 | 76.0 | 17.3 |
|  |  | 96 | 71.7 | 17.3 |
|  | D | 72 | 66.7 | 12.8 |
|  |  | 96 | 69.9 | 12.4 |

EXAMPLE 6

In this example, *Candida zeylanoides* IC 142, ATCC 20367 and No. 19-5, ATCC 20347 are each cultured on a malt extract agar slant prepared in the same manner as described in Example 1 at 30° C. for 24 hours. The resulting cultures are inoculated into 20 ml portions of a seed medium having the same composition as that of Example 2 in 250 ml-Erlenmeyer flasks provided with baffle plates and cultured with shaking at 200 r.p.m. at 30° C. for 24 hours. 2 ml portions of the thus prepared seed cultures are inoculated into 20 ml portions of a fermentation medium having the following composition in 250 ml-Erlenmeyer flasks provided with baffle plates.

| glucose | 20 g/L |
|---|---|
| calcium acetate monohydrate | 7.5 g/L |
| glycerin | 1 g/L |
| NH$_4$Cl | 5 g/L |
| KH$_2$PO$_4$ | 0.5 g/L |
| MgSO$_4$ . 7H$_2$O | 0.5 g/L |
| MnSO$_4$ . 4H$_2$O | 2 mg/L |
| ZnSO$_4$ . 7H$_2$O | 2 mg/L |
| FeSO$_4$ . 7H$_2$O | 1 mg/L |
| CuSO$_4$ . 5H$_2$O | 50 µg/L |
| thiamine hydrochloride | 100 µg/L |
| CaCO$_3$ (separately sterilized) | 10 g/L |
| (pH 6.0) | |

Fermentation is carried out with shaking at 200 r.p.m. at 30° C. for 96 hours while adding 29.4 g/L of calcium acetate monohydrate to the medium after 24, 48 and 72 hours of fermentation. The results are shown in Table 8.

TABLE 8

| Strains | Citric acid (mg/ml) | Isocitric acid (mg/ml) |
|---|---|---|
| IC 142, ATCC 20367 | 32.0 | 0.7 |
| No. 19-5, ATCC 20347 | 27.0 | 7.5 |

EXAMPLE 8

In this example, *Candida zeylanoides* IC 142, ATCC 20367 and No. 19-5, ATCC 20347 are each cultured on a malt extract agar slant prepared in the same manner as described in Example 1 at 30° C. for 24 hours. One loopful of the resulting cultures are inoculated into 20 ml portions of a medium comprising 150 g/L (as sugar) invertase-treated blackstrap molasses, 1 g/L NH$_4$Cl, 0.5 g/L MgSO$_4$.7H$_2$O, 1 g/L glycerin and 60 g/L CaCO$_3$ (pH 6.0) in 250 ml-Erlenmeyer flasks provided with baffle plates. Culturing is carried out with shaking at 200 r.p.m. at 30° C. for 120 hours. The results are shown in Table 9.

TABLE 9

| Strains | Citric acid (mg/ml) | Isocitric acid (mg/ml) |
|---|---|---|
| IC 142, ATCC 20367 | 85.0 | 1.5 |
| No. 19-5, ATCC 20347 | 70.0 | 8.2 |

As is illustrated from the above representative examples, the present invention provides for the selective production of citric acid.

What is claimed is:

1. A biologically pure culture of mutant yeast strain, *Candida zeylanoides* ATCC 20391, exhibiting growth substantially inferior to that of its parent strain in a minimum medium, but exhibiting growth comparable to that of its parent strain in a minimum medium including at least 0.1 mg/L of iron ion or iron-containing ion, said mutant being capable of producing citric acid.

2. A biologically pure culture of mutant yeast strain, *Candida zeylanoides* ATCC 20392, exhibiting growth substantially inferior to that of its parent strain in a minimum medium, but exhibiting growth comparable to that of its parent strain in a minimum medium including at least 0.1 mg/L of iron ion or iron-containing ion, said mutant being capable of producing citric acid.

3. A biologically pure culture of mutant yeast strain, *Candida zeylanoides* ATCC 20393, exhibiting growth substantially inferior to that of its parent strain in a minimum medium, but exhibiting growth comparable to that of its parent strain in a minimum medium including at least 0.1 mg/L of iron ion or iron-containing ion, said mutant being capable of producing citric acid.

4. A biologically pure culture of mutant yeast strain, *Candida zeylanoides* ATCC 20367, exhibiting growth substantially inferior to that of its parent strain in a minimum medium, but exhibiting growth comparable to that of its parent strain in a minimum medium including at least 0.1 mg/L of iron ion or iron-containing ion, and about 0.5 g/L of glycerin, said mutant being capable of producing citric acid.

* * * * *

UNITED STATES PATENT AND TRADEMARK OFFICE
CERTIFICATE OF CORRECTION

PATENT NO. : 4,322,498
DATED : March 30, 1982
INVENTOR(S) : KENICHIRO TAKAYAMA, et al.

It is certified that error appears in the above—identified patent and that said Letters Patent is hereby corrected as shown below:

On the cover page, add

--[30] Foreign Application Priority Data

Mar. 24, 1973  Japan  48-33089 --.

Signed and Sealed this

Second Day of August 1983

[SEAL]

Attest:

Attesting Officer

GERALD J. MOSSINGHOFF

Commissioner of Patents and Trademarks